United States Patent [19]

Chervenka et al.

[11] 4,181,700

[45] Jan. 1, 1980

[54] CENTRIFUGE TUBE SEQUENTIAL FRACTIONATOR

[75] Inventors: Charles H. Chervenka, Sunnyvale; Lee Gropper, Los Altos Hills, both of Calif.

[73] Assignee: Beckman Instruments, Inc., Fullerton, Calif.

[21] Appl. No.: 892,625

[22] Filed: Apr. 3, 1978

[51] Int. Cl.² .............................................. G01N 1/02
[52] U.S. Cl. .................................... 422/102; 422/72; 422/100; 233/1 R; 210/94; 210/515
[58] Field of Search ............. 23/259, 253 R; 233/1 R; 210/83, 94, 516, 515; 422/72, 102, 100

[56] References Cited

U.S. PATENT DOCUMENTS 4,003,834   1/1977   Coombs ................................. 23/259

OTHER PUBLICATIONS

Lammers, "Fractionation of Suspended and Colloidal Particles in Natural Waters", Report K-7749 (1968), Oak Ridge Gaseous Diffusion Plant, Tennessee.
Hill et al., "Apparatus for Collecting Fractions from Density Differential Interfaces and Its Use in Grav. Meas. of Total Myelin", Clin. Chem., vol. 16, No. 3 (1970), pp. 171-172.
Abdel-Latif, "Methods in Neurochemistry", vol. 5, p. 147 (1973).
Germain, "A Single Apparatus for Retrieving Density Gradients by Surface Tension", Anal. Biochem., vol. 57, pp. 89-92 (1974).
Rothschild, "Acid Phosphates in Amoeba Cell Fractions", C. R. Trav. Lab. Carlsberg, vol. 35, p. 457 (1967).
Bishop et al., "Red Cells in Density Gradients", Journal of Physics, vol. 67, p. 197 (1966).

*Primary Examiner*—R. E. Serwin
*Attorney, Agent, or Firm*—Robert J. Steinmeyer; Ferd L. Mehlhoff; William H. May

[57] ABSTRACT

A device for the sequential fractionation of the contents of a centrifuge tube containing centrifugally separated contents utilizing a syringe-like apparatus. The present invention utilizes removable syringe tips that are mounted on a chamber housing for extraction and retention of a precise volume of centrifuged fluid from the centrifuge tube. The syringe-like apparatus is mounted to a frame in such a manner that the chamber housing is movable relative to the plunger or piston to permit precise movement of the chamber housing with the removable syringe tip into the centrifuge tube for delicate and precise removal of the desired fraction of the fluid. The syringe tips are removed with each fraction that is collected from the contents in the centrifuge tube and can be placed in a storage rack for subsequent analysis.

13 Claims, 4 Drawing Figures

CENTRIFUGE TUBE SEQUENTIAL FRACTIONATOR

BACKGROUND OF THE INVENTION

The present invention is directed to sequential fractionation of the contents of a centrifuge tube after the centrifugation operation and, more particularly, is directed to a fractionation system that can remove very small fraction volumes accurately and reproducibly without undesirable mixing of the fractions or losses of the fractions in a transfer tube or line. The system operates without requiring a motor, pump or electrical power.

After the centrifugation process, it is necessary to remove fractions of the separated contents in the fluid which has been subjected to centrifugation in order to proceed with the proper analysis of each separated constituent or level of fluid density. When using very small centrifuge tubes, the removal of precise small volumes or fractions of the fluid material from the centrifuge tube without losses or remixing presents a significant problem.

Many types of devices have been developed for fractionating the contents of centrifuge tubes. One such approach utilized in a fractionation system is tube slicing whereby the tube is sequentially cut into segments in a special holder and knife assembly so that the fluid can be removed with a pipette from each segment after it is cut. Although tube slicing has been used with some success in separating the contents in extremely small test tubes into only two fractions, the system of tube slicing is entirely impractical and unsuccessful for small tube sequential fractionation process.

Another process utilized for tube fractionation is puncturing whereby the tube is pierced with a hollow needle and the contents within the tube are collected slowly drop by drop as a result of applying a slight pressure to a space at the top of the tube. Another method for tube fractionation is the concept of displacement with the tube contents being displaced upward through a special cap assembly by injecting a heavy density fluid into the bottom of the tube by the use of a puncturing needle or by the use of a long capillary placed down into the centrifuge tube.

A final primary method used in tube fractionation is aspiration whereby the tube contents are removed in sequential elements from the top of the tube. This is typically done by a syringe either hand held or in a special holder. Also a special assembly using a vacuum pump to withdraw fractions of the tube contents through a capillary placed into the open top of the tube enables fractionation by the aspiration principle.

Typically, the methods presently used for tube fractionation provide a somewhat satisfactory approach when using larger centrifuge tubes of 5 milliliters or greater capacity, since losses of the fluid due to leaks or retention in the tubing connections can be tolerated. However, with respect to very small centrifuge tubes such as one holding as small as 0.175 milliliters of fluid, these methods of tube sequential fractionation do not provide satisfactory results. The volumes of fluid being handled in such small centrifuge tubes are so minute that losses due to leaks or retention in the tubing or as a result of remixing cannot be tolerated.

SUMMARY OF THE INVENTION

The present invention is directed to a sequential fractionation system utilizing a syringe-like apparatus whereby a chamber housing is connected to a frame in such a manner that the housing can be moved very precise distances relative to a plunger or piston within the chamber of the housing. Attached to the chamber housing are removable syringe tips that are used to collect the precise volume of fluid material for each sequential fractionation step. The present invention utilizes no motors or pumps eliminating the need for electrical power. Further, there is no need for connection tubing which would result in possible loss of the fluid volume remaining residually in the tubing.

The principal unique feature of the present invention is the manner in which the syringe-like apparatus is used to withdraw aliquots of the fluid contained in the centrifuge tube. The syringe barrel incorporated into the chamber housing is moved downward relative to the syringe piston, which is restrained from moving downward by contact with the top plate of the fractionator. This is in contrast to the usual operation of syringes in which the piston is withdrawn from the barrel held in a fixed position. This novel mode of operation permits fluid aliquots to be removed from the centrifuge tube in a particularly advantageous manner as explained below.

No fluid can be drawn into the syringe tip until it contacts the surface of the fluid in the tube. The start of the collection event cannot be initiated until contact is established by the syringe tip on the fluid surface. As the syringe tip and barrel are lowered, fluid is continuously withdrawn into the syringe tip only from the very surface of the contents within the tube which is a completely different operation from the prior art use of a syringe where the tip is immersed within the fluid and the fraction is withdrawn from below the surface rather than on the surface. The present method is essential to obtain sharp separation of fractions and to avoid mixing with fluid further down in the tube.

To achieve the above described action of the present invention the volume swept out by the movement of the syringe barrel relative to the piston must be equal to or greater than the volume of the fraction to be collected. This requirement is best met by making the diameter of the syringe barrel slightly larger than the inside diameter of the centrifuge tube. If desired, the syringe barrel can be considerably larger than the tube diameter, but some air may be drawn into the syringe tip with the fluid volume. However, this will not adversely affect the accuracy of the volume of the fraction.

The volume of the fraction collected is determined and controlled by measuring the distance which the chamber housing containing the syringe barrel is moved relative to its piston. This measurement is made conveniently by use of an attached measuring device which can accurately measure the movement of the chamber housing. The relationship between the distance moved and the actual volume collected can be calculated from a knowledge of the inside diameter of the centrifuge tube, but it is more accurate and convenient to determine the relationship by weighing fractions collected by movement of the chamber housing a particular distance in a preliminary fractionation using a centrifuge tube filled with water.

When the desired volume of the fraction has been drawn into the syringe tip, the chamber housing containing the syringe barrel is now raised. Since the syringe piston is not restrained by contact with the top plate, the piston will move upward with the chamber housing. Thus, the fluid in the springe tip will remain in place undisturbed.

The second unique feature of this invention is the fact that each fraction is contained entirely within the syringe tip and there is absolutely no loss due to leaks or retention of fluid in tubing connections. By removal of the tip, the fraction can be quantitatively transferred for subsequent use or analysis.

DETAILED DESCRIPTION OF THE INVENTION

Figure 1:
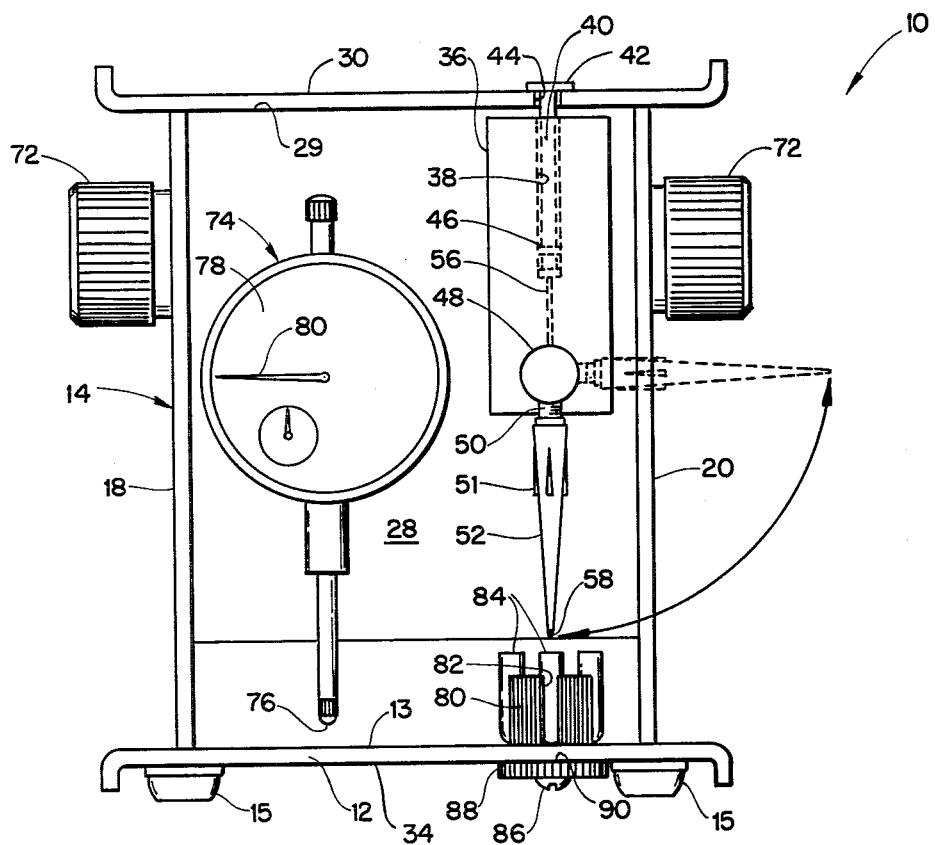
FIG. 1 is a front elevational view of the fractionation apparatus.

The fractionator device 10 of the present invention is shown in FIG. 1 having a base 12 on which is secured a frame member 14. At least three support pads or feet 15 are positioned in a balanced relationship on the bottom surface 34 of the base 12. As shown more clearly in FIG. 4, the frame member is an enlarged U-shaped one-piece member having a back portion 16 with integrally formed side panels 18 and 20 that extend perpendicular from the back portion 16. Located on the inside surface 22 of the side panels 18 and 20 and adjacent their free edges 24 are travel grooves 26. As shown in FIG. 1, a top plate 30 is secured over the frame member 14.

The travel grooves 26 are designed to receive a travel plate 28 that operates in a manner which will be discussed below. Securely mounted to the travel plate 28 in FIG. 1 is a chamber housing or hollow vessel 36 having an inner chamber 38 designed to receive a piston 40 or plunger 40. The piston or displacement member has a flanged exterior end 42 which is larger than an aperture 44 in the top plate 30, so that movement of the piston 40 toward the base 12 is limited by the flanged end 42 contacting the top plate 30. The piston 40 has a head portion 46 which is designed to ride in sealing engagement within the cylindrical interior of the chamber 38.

Figure 2:
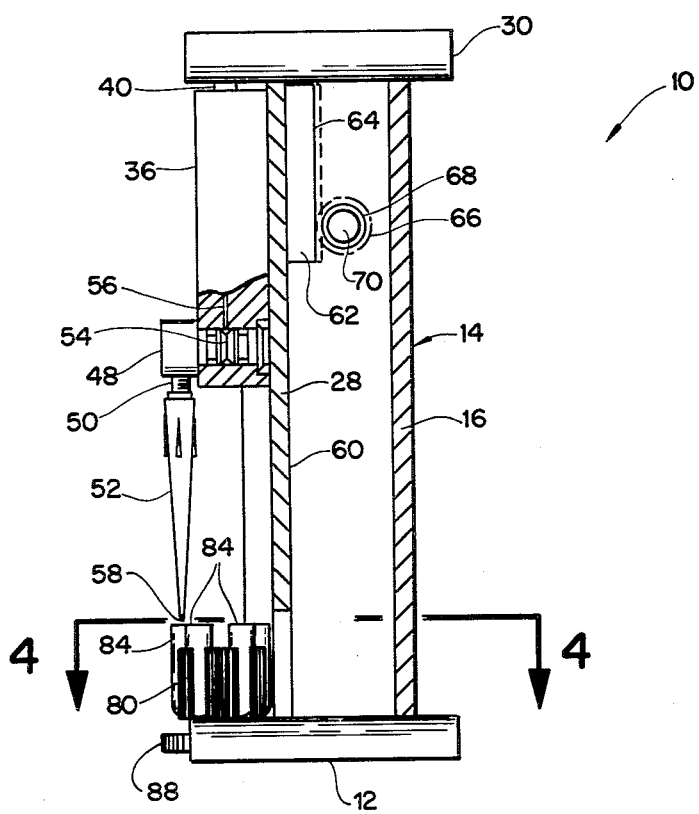
FIG. 2 is a partial sectional side elevational view of the apparatus.
Figure 3:
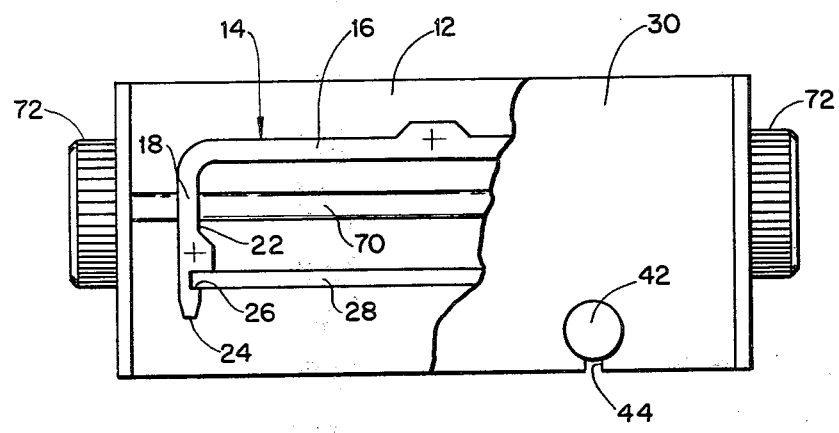
FIG. 3 is a top partial sectional view of the fractionation apparatus.

As shown in both FIGS. 1 and 2, a swivel mounting or head 48 is attached to the chamber housing 36. The mounting 48 is designed to rotate annularly with respect to the housing 36 in FIG. 1. A coupling 50 is located on the swivel mounting and is designed to receive a removable syringe tip 52. The swivel mounting 48 has a junction arrangement 54 to rotatably affix the mounting on the chamber housing 36. The junction arrangement 54 is designed in such a manner to allow fluid communication between the coupling 50 of the swivel mounting 48 and the passage 56 which is in fluid communication with the cylindrical chamber 38 in which the piston 40 resides. Consequently, there is fluid communication between the open end 58 of the syringe tip 52 and the cylindrical chamber 38 within the chamber housing 36. The swivel mounting 48 is designed as shown in FIG. 1 to provide for more convenient insertion and removal of the syringe tip 52 as will be explained.

As shown in FIG. 2, located on the rear surface 60 of the travel plate 28 is a rack gear 62 having a plurality of teeth 64. Located in contacting relation with the rack gear teeth 64 is a pinion gear 68 having pinion gear teeth 66. The pinion gear 68 is rigidly mounted to a drive shaft 70 which is positioned and supported on and between the side panels 18 and 20 of the frame 14. Consequently, rotational movement of the drive shaft 70 will cause a corresponding movement of the rack gear 62 with the travel plate 28 which rides within the slots 26 of the side panels 18 and 20 of the frame 14. Located on each end of the drive shaft 70 are control knobs 72 which are designed to provide more accurate control movement of the travel plate 28 with the chamber housing 36 and syringe tip 52. Biasing means (not shown are used on the drive shaft to provide a slight resistance to the rotation of the knobs to enhance precise movement of the travel plate.

Also secured to the travel plate 28 as shown in FIG. 1 is a dial micrometer 74 having a gauge reference end 76 and a scaled measuring face 78 with rotatable indicator dial 80. Consequently, downward movement of the travel plate 28 will result in the gauge end 76 of the micrometer contacting the top surface 13 of the base 12.

Figure 4:
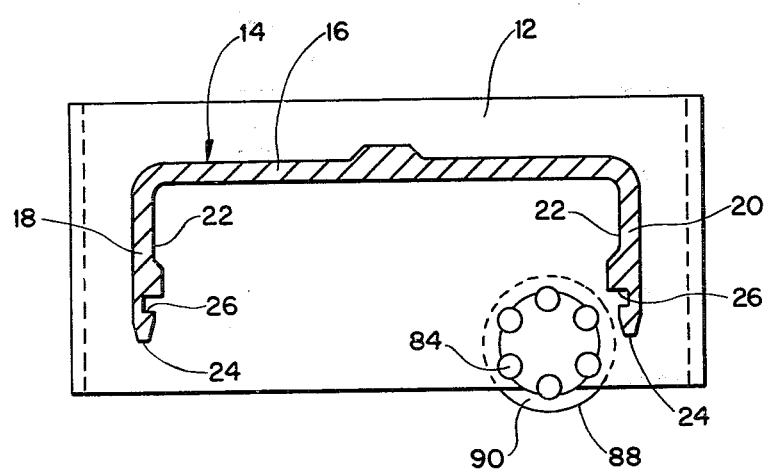
FIG. 4 is a sectional view taken along the lines 4—4 in FIG. 2.

Rotatably mounted on the base 12 in FIGS. 2 and 4 is a centrifuge tube holder 80 having a plurality of cavities 82 designed to receive a plurality of centrifuge tubes 84. The cylindrical holder 80 is connected to the base 12 by a screw or bolt 86 which also connects an indicator dial 88 to the base 12. Indicia 90 on the indicator dial wheel 88 are to identify and reference each of the centrifuge tubes 84.

Turning to the operation of the present fractionation system 10, attention is directed to FIGS. 1 and 2. After centrifugation of a series of fluid samples has been completed, the centrifuge tubes 84 are placed within the respective apertures 82 in the tube holder 80 of the fractionator 10. The travel plate 28 is positioned in its upper location with the top edge of the travel plate 29 being closely adjacent the top plate 30 of the device 10. A pipette or syringe tip 52 having a series of ribs 51 for easier grasping is inserted on the coupling 50 of the swivel head 48 that is connected to the housing 36. As shown in FIG. 1, the swivel mounting 48 is pivoted essentially to the position shown in phantom whereby the syringe tip can be more easily snapped into place over the coupling 50. The syringe tip, once securely placed on the swivel mounting 48, is rotated down to the vertical position as shown in solid lines in FIG. 1. The operator uses the control knobs 72 of the drive shaft 70 to rotate the pinion gear 68 to move the rack gear 62 and the travel plate 28 in a direction toward the base 12 of the device. When the operator notes that the open end 58 of the syringe tip 52 barely comes in contact with the top surface of the fluid contents in the test tube 84, the operator records the reading on the micrometer scale 78. By precise movement of the control knobs 72 the operator moves the syringe tip into the fluid noting the differential reading on the micrometer scale. When the reading on the scale corresponds to the precise volume desired, downward movement of the syringe tip is stopped.

Because the flanged end 42 of the plunger or piston 40 is restrained by the top plate 30 of the device, the downward movement of the chamber housing 36 in conjunction with the stationary piston head 46 will create a slight vacuum within the chamber 38. Further, the chamber 38 is made slightly larger than the size of the centrifuge tube 84 to enhance the creation of negative pressure in the chamber. Corresponding negative pressure which is caused within the chamber 38 will provide for the extraction of the fluid from the tube 84 as the syringe tip is lowered into the centrifuge tube. The fluid is withdrawn into the syringe tip off the very top surface of the level of contents of the tube. This alleviates any possible disturbance of subsequent fractions. Therefore, as the syringe tip is lowered, only the very top surface of the fluid is continually removed.

Once the desired volume of fluid is received within the syringe tip 52, the control knobs 72 are used to raise the travel plate 28 and retract the syringe tip 52 from within the test tube 84. It should be noted that, as the chamber housing 36 is raised with the travel plate, the flanged end 42 of the piston 40 is also raised above the top plate 30 so that the fluid is not extracted from the syringe tip as it is being raised. The operator then moves the syringe tip 52 to the horizontal position shown in phantom in FIG. 1 and gently removes the syringe tip for placement in a storage rack. In addition to the convenience provided in the removal of the syringe tip, this horizontal position also prevents the fluid in the tip from running out as the tip is removed.

A new syringe tip 52 is connected to the coupling 50 and the process repeated by extracting the next desired fraction from the contents within the centrifuge tube. Once all of the desired contents have been removed from the centrifuge tube, indicator plate 88 is rotated one notch to the next centrifuge tube to bring it in alignment with the syringe tip and the fractionation sequence is repeated on the full contents of another test tube.

Although the present invention is directed primarily to a fractionation device providing accurate and reproducible fractionation of fluid in a very small or extremely small test tube, the overall device could be scaled larger in size with increasing diameter of the chamber 38 so that it could be used for larger centrifuge tubes in density gradient experiments, for example, in conjunction with swinging bucket rotors and preparative ultracentrifuges. This device would provide the necessary fractionation with extreme simplicity, accuracy and convenience as compared to prior art fractionation systems.

The present invention describes a fractionation system device which allows for the fractionating of the contents in extremely small centrifuge tubes by the use of a simple mechanism that provides ultimate convenience and accuracy without the disadvantages of utilizing motors, pumps or electrical power as well as any connecting tube lines. The present invention is extremely versatile in the number of fractions collected and their size can be varied over a considerable range.

What is claimed is:

1. A tube fractionator assembly for the sequential fractionation of centrifugated contents in a centrifuge tube, said assembly comprising:
    a housing having an enclosed chamber for receipt of a plunger for relative movement with respect to said housing;
    means for mounting said housing in a vertical orientation;
    means on said mounting means for moving said housing relative to said plunger in one direction; and
    means removably mounted on said housing for extracting and for holding a precise portion of said contents, said extracting and holding means with said precise portion of said contents being removable from said housing to store said precise portion of said contents for later analysis.

2. A fractionator assembly for the sequential fractionation of centrifugated contents in a centrifuge tube, said assembly comprising:
    a frame structure;
    a hollow vessel movably connected to said frame, said vessel having an enclosed chamber;
    a volume displacement member movable within said vessel chamber;
    means for moving said vessel relative to said frame;
    means on said frame for limiting movement of said displacement member as said vessel moves in one direction;
    means on said frame for supporting said tube below said vessel; and
    means connected to said vessel for receiving and retaining a fraction of said contents from said tube as said vessel is moved relative said frame in said one direction, said receiving and retaining means acting in conjunction with said hollow vessel and said moving means to extract fluid only from the surface of said contents in said tube and to hold said fluid therein, said receiving and retaining means removable from sad housing to provide a storage container for said fluid separate from said assembly.

3. A fractionator assembly as defined in claim 2, wherein said hollow vessel comprises a housing having a cylindrical chamber.

4. A fractionator assembly as defined in claim 3, wherein said chamber has a diameter larger than said centrifuge tube.

5. A fractionator assembly as defined in claim 3, wherein said volume displacement member comprises a piston slidably mounted within said chamber.

6. A fractionator assembly as defined in claim 3, wherein said receiving and retraining means comprises a removable syringe tip mounted on said housing.

7. A fractionator assembly as defined in claim 6 and additionally comprising a swivel mounting located on said housing with a coupling for receipt of said syringe tip.

8. A fractionator assembly as defined in claim 7, wherein said swivel mounting being pivotal with respect to said housing to permit removal and connection of said syringe tip with respect to said coupling with said syringe tip in a nonvertical orientation.

9. A fractionator assembly as defined in claim 2, wherein said moving means comprises:
    a travel plate; and
    gear means for moving said plate.

10. A fractionator assembly as defined in claim 9 wherein said gear means comprises a rack gear on said travel plate and a pinion gear.

11. A fractionator assembly as defined in claim 10 and additionally comprising a drive shaft mounted on said frame adjacent said travel plate, said pinion gear located on said drive shaft in contacting relation with said rack gear.

12. A fractionator assembly as defined in claim 2, wherein said limiting means comprises a top plate on said frame, said top plate having a slot for receipt of said displacement means and for holding said displacement means in a fixed position relative to said movement of said vessel in said one direction.

13. A fractionator assembly as defined in claim 2 and additionally comprising scale means for measuring the travel of said hollow vessel in said one direction.

* * * * *